United States Patent [19]

Fischer, Jr.

[11] Patent Number: 5,544,648
[45] Date of Patent: Aug. 13, 1996

[54] DEVICE FOR INTRATRACHEAL VENTILATION AND INTRATRACHEAL PULMONARY VENTILATION INCLUDING REVERSE VENTURI

[75] Inventor: Frank J. Fischer, Jr., Bloomington, Ind.

[73] Assignee: Cook Incorporated, Bloomington, Ind.

[21] Appl. No.: 440,533

[22] Filed: May 12, 1995

[51] Int. Cl.$^6$ ................................................ A61M 16/00
[52] U.S. Cl. ........................ 128/207.14; 128/207.15
[58] Field of Search ........................... 128/207.14, 207.15

[56] References Cited

U.S. PATENT DOCUMENTS

| | | | |
|---|---|---|---|
| 4,265,235 | 5/1981 | Fukunaga | 128/200.24 |
| 4,463,755 | 8/1984 | Suzuki | 128/204.18 |
| 4,508,117 | 4/1985 | Rodari | 128/204.21 |
| 4,646,733 | 3/1987 | Stroh et al. | 128/207.16 |
| 4,850,371 | 7/1989 | Broadhurst et al. | 128/207.15 |
| 4,976,261 | 12/1990 | Gluck et al. | 128/207.14 |
| 5,186,167 | 2/1993 | Kolobow | 128/207.14 |
| 5,291,882 | 3/1994 | Makhoul et al. | 128/207.14 |
| 5,452,715 | 9/1995 | Boussignac | 128/207.15 |

*Primary Examiner*—Aaron J. Lewis
*Attorney, Agent, or Firm*—Richard J. Godlewski

[57] ABSTRACT

A device (10, 80 or 120) for creating a sub-atmospheric pressure near the carina (12) of a human or veterinary patient (48) includes a channel (28) or perforation (92 or 132) for the passage of an oxygen-containing gas therethrough, the channel (28) or perforation (92 or 132) being open in a direction distal of the patient, so as to establish a zone (30, 94 or 142) of sub-atmospheric pressure by reverse venturi effect during patient exhalation. The sub-atmospheric pressure in the zone (30, 94 or 142) facilitates removal of carbon dioxide from the lungs (54) of the patient and permits intratracheal and/or intratracheal pulmonary ventilation to be performed at pressures less than those conventionally required for such ventilation. The device (10, 80 or 120) of the present invention is also advantageous in obviating the risks inherent in prior reverse venturi devices, specifically, the possibility of detachment of a tubular member in those devices, and the possible complications of surgical recovery of the tubular member from the bronchi (52) or lungs (54) of the patient (48). The device (10, 80 or 120) of the present invention achieves this latter advantage either by eliminating the tubular member of prior reverse venturi devices, or by providing a shoulder (130) affirmatively preventing distal movement and loss of it.

22 Claims, 5 Drawing Sheets

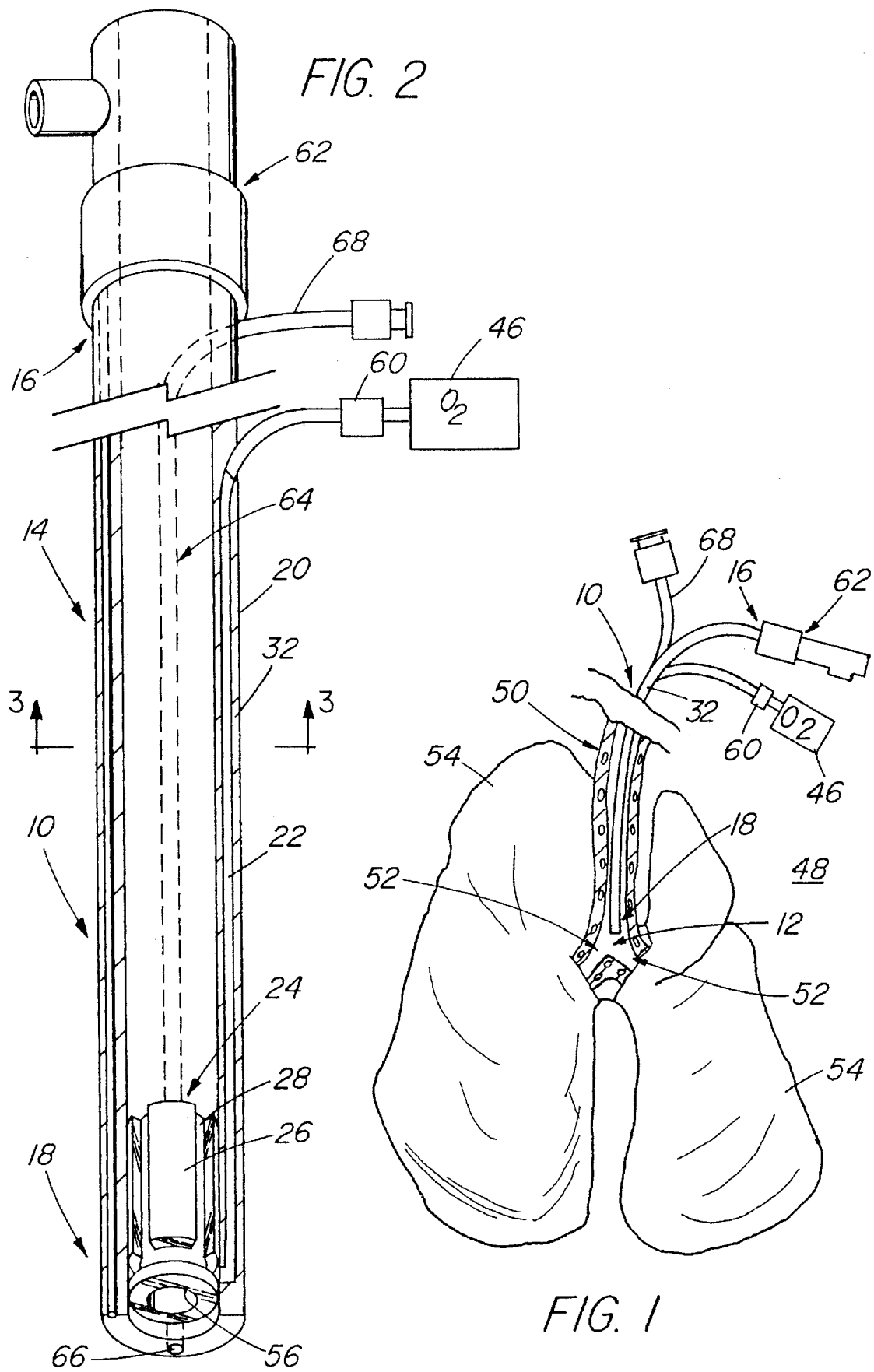

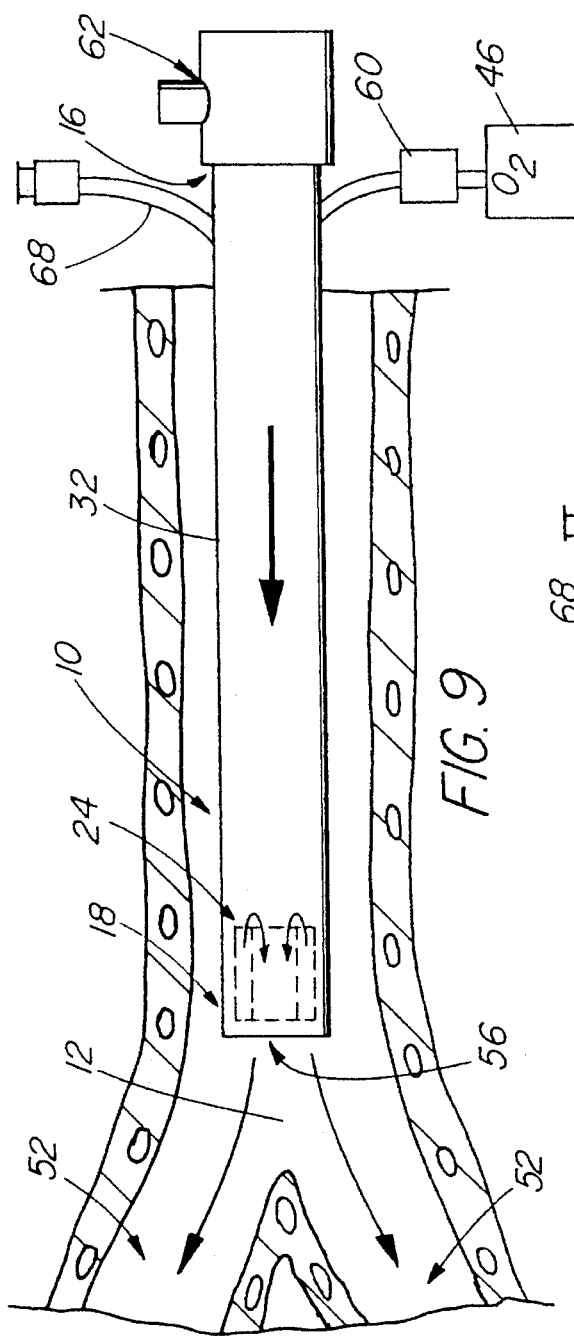
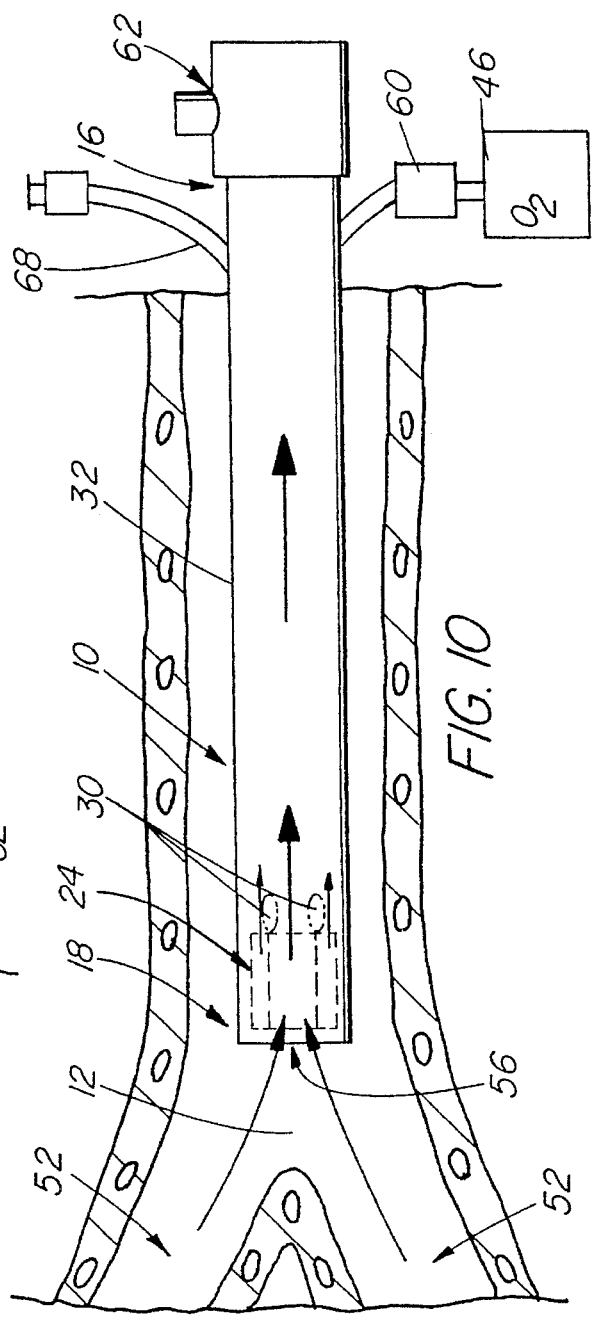

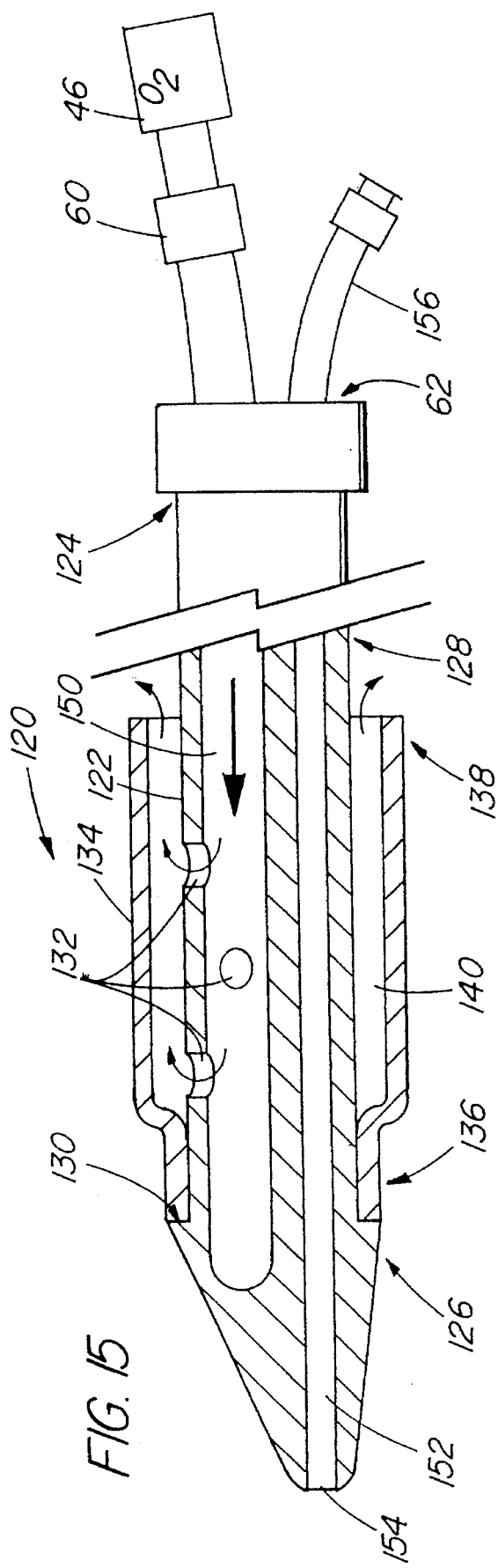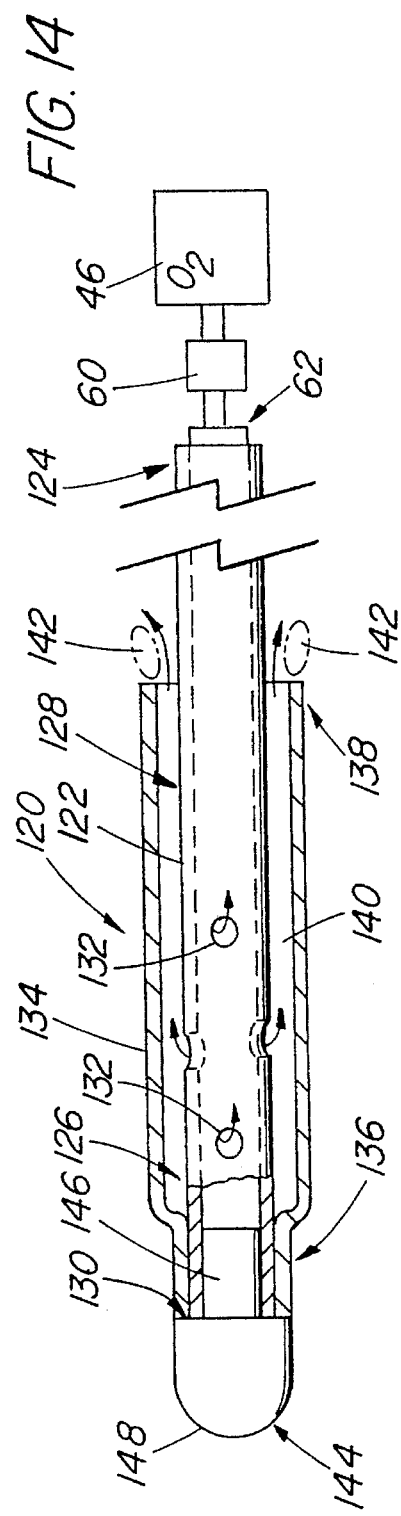

DEVICE FOR INTRATRACHEAL VENTILATION AND INTRATRACHEAL PULMONARY VENTILATION INCLUDING REVERSE VENTURI

TECHNICAL FIELD

This invention relates generally to medical devices, and more particularly to devices for delivering fresh air, oxygen or an oxygen-containing gas to the trachea and lungs of a human or veterinary patient.

BACKGROUND OF THE INVENTION

Mechanical ventilation has long been used to support lung function in a patient, and entails the use of warmed and moistened fresh air, oxygen, or an oxygen-containing gas (such as an anesthetic gas) supplied to the patient under pressure for oxygenating the patient's lungs. One known method of mechanical ventilation is intratracheal ventilation (ITV). ITV involves the delivery of a warmed and well-humidified gas at or near the patient's carina (the fork of the trachea leading to the bronchial tubes). The gas is delivered through a ventilator tube positioned in the trachea. The ventilator tube can be a catheter, a tracheal tube, an endotracheal tube or the like, and the oxygen-containing gas can be supplied through it on either a continuous or periodic basis. In the former case, the ventilator tube can be supplied with a positive end expiratory pressure (PEEP) valve, whose periodic activation allows air from the lungs (enriched in carbon dioxide) to exit the patient's body.

While they do provide some degree of oxygenation when initially employed, the continued use of mechanical ventilators for ITV is subject to significant drawbacks. For example, mechanical ventilators have traditionally been required to deliver high gas pressures, in order to achieve adequate oxygenation. There are several reasons for this. When a mechanical ventilator is first installed, the interior of the ventilator tube usually contains just air, rather than an oxygen-enriched gas; when activated, this air is pushed into the lungs, while the oxygen-enriched gas remains outside the lungs. The alveoli in the patient's lungs expire carbon dioxide, and the expired carbon dioxide builds up in the lungs after several ventilation cycles, because the high pressure of the oxygen-enriched gas—and any straight air between the gas and the carbon dioxide in the lungs—prevents at least some of the carbon dioxide from escaping the lungs. The elevated level of carbon dioxide leads the health practitioner to supply even higher pressures of the oxygen-enriched gas to the ventilator tube. After a time as short as only a few hours, the patient's lungs may suffer damage from two sources, specifically, the elevated ventilator pressure, and the build-up of carbon dioxide. The result can be hypoxia, respiratory acidosis, hypercarbia, iatrogenic lung damage, pulmonary hypertension, overinflation, and/or pulmonary parenchymal injury. These problems can even be severe enough to result in the death of the patient. Further, while these problems are more likely to occur and to be more severe in patients with significantly impaired lung function (such as pediatric patients and patients who have undergone a partial lung removal), these problems can even occur in patients with healthy lungs.

Another known method of mechanical ventilation is intratracheal pulmonary ventilation (ITPV). ITPV similarly involves the delivery of an oxygen-containing gas at or near the patient's carina. The gas is continuously supplied either at a constant pressure, or by pressure pulses at a frequency of about 1 to 50 cycles per second. One drawback to this method is that carbon dioxide outflow is periodic or intermittent, controlled by relatively complex valve and timer mechanisms. As a result, the potential remains for an inadequate expiration of carbon dioxide and a resultant progressive build up of the carbon dioxide level in the patient. Additionally, the cyclical peak pressures typically employed in this method are high, often significantly higher than the pressures employed in ITV. Accordingly, all of the problems which may be encountered in the use of ITV may also be faced during the use of ITPV.

One solution to these and other problems has been the Kolobow reverse thrust catheter, such as disclosed in U.S. Pat. No. 5,186,167 (Feb. 16, 1993). The disclosure of that patent is expressly incorporated by reference herein. By way of summary, the Kolobow device has a catheter preferably contained in a tracheal or endotracheal tube. The catheter includes a plurality of ports through its distal end, the distal end of the catheter being positioned at or near the patient's carina. Air supplied through the catheter diffuses transversely through the ports, creating zones of sub-atmospheric pressure which facilitate removal of carbon dioxide-laden air from the patient's lungs. The particular embodiment shown in FIG. 3C in the patent includes a tubular portion 19 on the catheter tip 16 which defines an annular exit port 17, directing the flow of air and oxygen in a direction opposite the distal end 18 of the catheter. The patent notes at column 8, lines 4 through 14, that while it is preferred that the exit port is annular, it is not necessary to employ a port having the specific shape of an annulus; rather, the essential feature is to provide a means which directs the air and oxygen in a direction opposed to the distal end 18 of the catheter tip 16. Although not described in such terms in the patent, the low pressure zones are produced by the well-known venturi effect. For convenience, since the flow creating the venturi effect is directed opposite to the incoming flow of air and oxygen, devices of this type will be referred to herein as "reverse venturi devices."

The Kolobow or reverse venturi device functions quite well to move carbon dioxide-laden air out of the patient's lungs through the tracheal or endotracheal tube, thus improving oxygenation in comparison to that achieved with other ITV and ITPV devices. Moreover, this improved oxygenation is achieved at pressure levels significantly lower than the pressures employed in other ventilation devices, substantially reducing the risk of trauma to the patient from elevated ventilation pressures.

Unfortunately, the Kolobow or reverse venturi device (at least, insofar as actually constructed in practice) potentially presents a different risk to the patient. In the device, the catheter tip 16 causing the venturi effect is generally of solid material and is pressed over and attached to the distal end of a hollow and flexible catheter. As a practical matter, such attachment is problematic, due to the nature of the materials used and the small dimensions encountered. The result is that the catheter tip 16 may loosen and separate from the distal end of the catheter, and be deposited in one of the bronchi or lungs of the patient. As a result, the catheter tip 16 may damage the tissue of the lung and create complications such as fluid pockets, infections and patient discomfort. Furthermore, the separated catheter tip 16 may require surgical removal, and the complications attendant to lung surgery.

SUMMARY OF THE INVENTION

The foregoing problems are solved and a technical advance is achieved in an illustrative reverse venturi device for creating a sub-atmospheric pressure near the carina of a human or veterinary patient, employed for intratracheal and/or intratracheal pulmonary ventilation. The device is a reverse venturi device, generally of the type disclosed by Kolobow, but which in any of several ways prevents or avoids the complications which might arise from separation of the catheter tip 16 of Kolobow. More particularly, the present invention is directed to a device for creating a sub-atmospheric pressure near the carina of a human or veterinary patient, which includes a channel or perforation for the passage of an oxygen-containing gas therethrough, the channel or perforation being open in a direction distal of the patient, so as to establish a zone of sub-atmospheric pressure by reverse venturi effect during patient exhalation. "Sub-atmospheric pressure" means a pressure below at least the air pressure within the lungs and bronchi at the start of patient exhalation, and is preferably a pressure below the ambient atmospheric pressure.

The sub-atmospheric pressure created in the present invention is advantageous in that it facilitates removal of carbon dioxide from the lungs of the patient and permits intratracheal and/or intratracheal pulmonary ventilation to be performed at pressures less than those conventionally required for such ventilation. The device of the present invention is also advantageous in obviating the potential risks in prior reverse venturi devices of the type disclosed in the Kolobow reference, specifically, the possibility of detachment of the tubular member in those devices, and the possible complications of surgical recovery of the tubular member from the bronchi or lungs of the patient. The device of the present invention achieves this latter advantage either by completely eliminating the tubular member 19 of Kolobow and similar reverse venturi devices, or by providing a shoulder affirmatively preventing distal movement and loss of it.

In a first aspect, then, the present invention is directed to a device for creating a sub-atmospheric pressure near the carina of a human or veterinary patient, which comprises a tracheal or endotracheal tube having proximal and distal ends, a wall connecting them, and a passageway for the flow of an oxygen-containing gas; and which also comprises an insert received in and circumferentially abutted by the distal end of the tracheal or endotracheal tube, the insert having a surface defining at least one channel in communication with the passageway of the tube, the channel being open towards the proximal end of the tube; such that a zone of sub-atmospheric pressure is established, inside the tube and adjacent the distal end of the tube during exhalation of the patient, upon passage of an oxygen-containing gas through the tube passageway and the at least one channel of the insert.

Preferably, the tracheal or endotracheal tube is a multiple lumen tube, in which the passageway is formed in the wall of the tube and includes an outlet adjacent the distal end of the tube. Also preferably, the insert is shaped as a hollow cylinder having a plurality of axial channels and a circumferential channel connecting the axial channels to the passageway outlet at the distal end of the tube. Advantageously, the inner surface of the wall of the tube and the outer surface of the insert together define the at least one channel. The device can further comprise a source of an oxygen-containing gas, preferably a continuous source of such a gas, connected to the passageway of the tube.

This aspect of the invention is particularly advantageous over the device disclosed by Kolobow in that it renders the tubular portion 19 of Kolobow unnecessary, thereby affirmatively preventing any risk of separation of that portion from the catheter and its loss inside the patient, thus avoiding any potential trauma or complications from procedures needed to recover it.

Furthermore, the tracheal or endotracheal tube advantageously includes a second passageway in the wall of the tube, which has an outlet distal of the insert. This second passageway is utilized for infusing drugs, but more importantly, monitoring the pressure at the distal end of the tube and/or near the carina of the patient.

In a second aspect, the present invention is directed to a device having the same purpose, but which instead comprises a catheter having proximal and distal ends, as well as a sidewall extending between the catheter ends, the sidewall having an external surface; and which further comprises at least one perforation through the catheter sidewall near the distal end of the catheter; wherein the at least one perforation is acutely angled with respect to the external surface of the catheter sidewall, such that a zone of sub-atmospheric pressure is established, outside the catheter adjacent its distal end during patient exhalation, upon passage of an oxygen-containing gas through the catheter and the at least one perforation.

Preferably, a plurality of the perforations are formed by slits cut into the external surface of the catheter sidewall, the slits being cut at an angle of less than 45 degrees with respect to the external surface of the sidewall, more preferably at an angle of no more than about 30 degrees. Also preferably, the catheter sidewall is constructed of a nylon radiopaque material tubing, or a material having an equivalent flexibility. Advantageously, the device can further comprise a tracheal or endotracheal tube in which the catheter is positioned, and/or a source of an oxygen-containing gas connected to the proximal end of the catheter.

This aspect of the invention is similarly advantageous over the device disclosed by Kolobow in that it renders the tubular portion 19 of Kolobow unnecessary, and similarly avoids any potential complications from its separation or procedures needed to recover it. Additionally, in the second aspect of the invention, the catheter includes a passageway in the sidewall thereof with an outlet distal of the at least one perforation for advantageously monitoring the pressure near the carina of a patient.

In a final aspect, the present invention is directed to a device for creating a sub-atmospheric pressure near the carina of a human or veterinary patient, which comprises a catheter having proximal and distal ends, and an exterior surface extending between them, the catheter having a defined diameter near its distal end, and the distal catheter end having a shoulder extending radially outward of the catheter a distance greater than the defined diameter; which also comprises at least one radial perforation through the catheter, located adjacent the distal end of the catheter but between the proximal catheter end and the shoulder on the distal catheter end; and which further comprises a tubular member positioned about the exterior catheter surface and extending over the at least one radial perforation, the tubular member including a distal end abutting the shoulder on the distal end of the catheter and which is substantially sealed to the external surface of the catheter, and the tubular member also including a proximal end opposite the distal end of the member having an interior diameter greater than the defined diameter of the catheter, so as to provide a gap between the tubular member and the exterior surface of the catheter, such that a zone of sub-atmospheric pressure is established, outside the catheter adjacent its distal end during patient exhalation, upon passage of an oxygen-containing gas through the catheter, the at least one perforation, and the gap between the tubular member and the exterior surface of the catheter.

Preferably, the shoulder on the distal end of the catheter is annular in shape, and is formed by a plug received in and sealed to the distal end of the catheter. Also preferably, the tubular member is formed of shrink-wrap tubing, and is shrunk at its distal end about the exterior surface of the catheter. Advantageously, the device can further comprise a tracheal or endotracheal tube in which the catheter is positioned, and/or a source of an oxygen-containing gas connected to the proximal end of the catheter.

This aspect of the invention is particularly advantageous over the device disclosed by Kolobow in that the shoulder affirmatively prevents any risk of separation of the tubular member from the catheter, and thus its loss inside the patient, thereby avoiding any potential complications from such loss and procedures needed to recover it. Furthermore, in the final aspect of the invention, the catheter includes a passageway with an outlet distal of the at least one perforation for advantageously monitoring pressure near the carina of the patient.

The reverse venturi device of the present invention can be used in replacement of the device disclosed in the Kolobow patent, in any of the methods and in combination with any of the other apparatus disclosed in that patent, subject to the good medical judgment of those skilled in this area. The whole of the disclosure of that patent; particularly the portion cited below, is expressly incorporated by reference herein.

BRIEF DESCRIPTION OF THE DRAWING

A better understanding of the present invention will now be had upon reference to the following detailed description, when read in conjunction with the accompanying drawing, wherein like reference characters refer to like parts throughout the several views, and in which:

FIG. 1 is a perspective view of a first preferred embodiment of the present invention positioned in the trachea of a patient;

FIG. 2 is a side exploded view of the embodiment shown in FIG. 1;

FIGS. 9 and 10 are schematic views of the use of the first preferred embodiment of the present invention;

FIG. 14 is a partial view of another preferred embodiment of the present invention; and FIG. 15 is a partial view of another aspect of the embodiment of FIG. 14.

DETAILED DESCRIPTION

Figure 3:
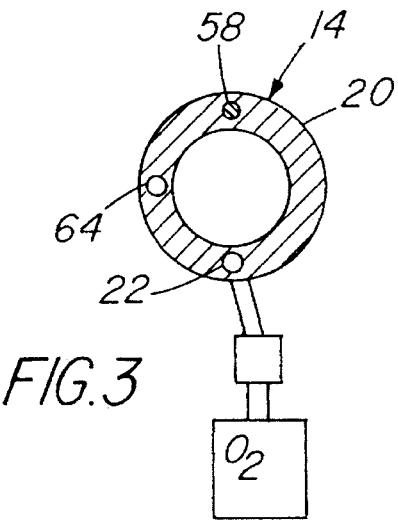
FIG. 3 is a cross-sectional view taken along line 3—3 of FIG. 2.
Figure 4:
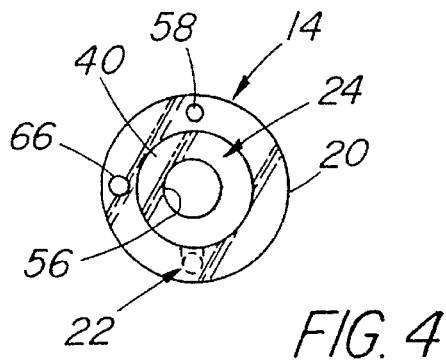
FIG. 4 is an end view of the first preferred embodiment of the present invention.
Figure 7:
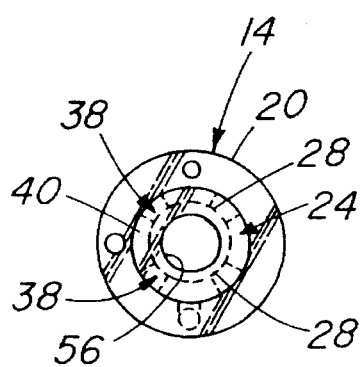
FIG. 7 is an end view taken from line 7—7 of FIG. 5.
Figure 5:
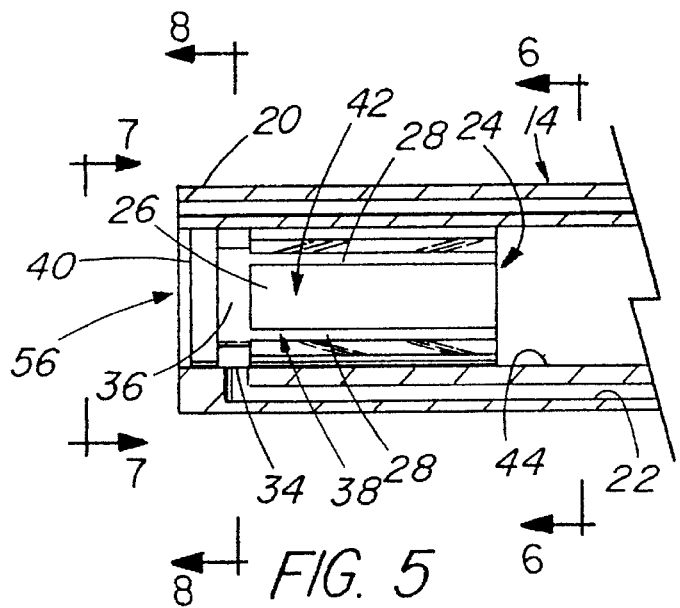
FIG. 5 is a partial view of a portion of the first preferred embodiment of the present invention.
Figure 8:
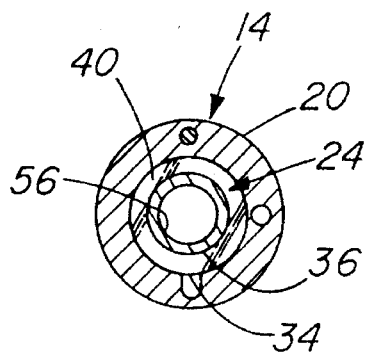
FIG. 8 is a cross-sectional view taken along line 8—8 of FIG. 5.
Figure 6:
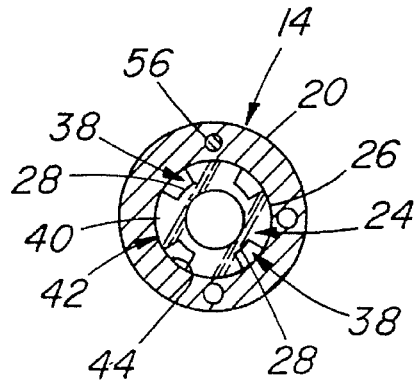
FIG. 6 is an end view taken from line 6—6 of FIG. 5.

With reference first to FIGS. 1 and 2, the first preferred embodiment of the present invention for creating a subatmospheric pressure near the carina 12 of a human or veterinary patient 48 is thereshown as a device 10, extending from outside the patient 48 to a location within the trachea 50 of the patient 48. The carina 12 is, of course, the location at which the bronchi 52 split from the trachea 50, and lead towards the lungs 54 of the patient 48.

More particularly, the device 10 first comprises a tracheal or endotracheal tube 14 having a proximal tube end 16 positioned outside the trachea 50 of the patient 48, and a distal tube end 18 spaced from the proximal tube end 16 and positioned at or near the carina 12 of the patient 48. The tube 14 includes a tube wall 20 connected to and extending between the proximal tube end 16 and the distal tube end 18, as well as a tube passageway 22 for the flow of an oxygen-containing gas therethrough. The tube 14 is preferably a conventional multiple lumen tracheal or endotracheal tube 32, in which the tube passageway 22 (normally used for the application of suction to remove fluids) is embedded in the tube wall 20 and is connected by an appropriate valve and/or monitoring mechanism 60 to a source 46 of the oxygen-containing gas, such as warmed and moistened air, oxygen, gaseous anaesthetic, or the like. The proximal tube end 16 is attached to a fitting or connector 62, and thence to valves, regulators, monitors or controls (not shown) suitable to the particular ventilation method to be employed. It is highly desirable that tube 14 include a second passageway 64 in the wall thereof, which has an outlet 66 distal of insert 24 for infusing drugs and/or monitoring pressure near the carina of the patient. A side arm 68 with a well-known Luer lock connector communicates with second passageway 64 near the proximal end 16 of the tube 14. Of course, it is highly desirable that the tube 14 also include a line of radiopaque material 58 in the tube wall 20 and running the entire length of the tube wall 20, to facilitate monitoring of the position of the tube 14 in the trachea 50 of the patient 48. The positions of the second passageway 64, the line of radiopaque material 58, and the tube passageway 22 are more clearly shown in FIG. 3.

With continued reference to FIG. 2, but especially with further reference to FIGS. 4 through 8, the device 10 also comprises an insert 24 received in and circumferentially abutted by the distal tube end 18, for providing the reverse venturi flow of the oxygen-containing gas through the tube 14. More particularly, the insert 24 has a surface 26 defining at least one insert channel 28 in fluid communication with the tube passageway 22, the at least one insert channel 28 being open towards the proximal tube end 16. Preferably, when the tube passageway is formed in the tube wall 20, the tube passageway 22 includes a passageway outlet 34 located adjacent the distal tube end 18, and the at least one insert channel 28 is in fluid communication with the passageway outlet 34. Also preferably, the at least one insert channel 28 comprises a plurality of channels, and more particularly, at least one circumferential channel 36 in fluid communication with the passageway outlet 34, and a plurality of axial channels 38 connected to the tube passageway 34 by the at least one circumferential channel 36.

The insert 24 is most preferably configured as a hollow cylinder 40 having a central throughbore 56, although any of a variety of other shapes for the insert 24 might be suitable, if the material of the tube 14 is sufficiently flexible to ensure an adequate seal to the insert 24, and if a central passage is provided to allow the exit of carbon-dioxide enriched air from the lungs 54, and out through the bronchi 52 and trachea 50. Also preferably, it is the outer surface 42 of the cylinder 40 that is the insert surface 26 on which the at least one insert channel 28 is formed. In such a case, the at least one insert channel 28 is further defined by the inner surface 44 of the tube wall 20, at the distal tube end 18.

The insert 24 may be composed of any suitable medical grade material, such as a sterilizeable synthetic. However, as the tube 14 will typically be composed of a material which is somewhat flexible, it is highly desirable that the insert 24 be composed of a material which is more rigid than the material making up the tube 14; this ensures that the inner surface 44 of the tube wall 20 does not collapse into the at least one insert channel 28, and prevent the flow of the oxygen-containing gas through the at least one insert channel 28. It is therefore advantageous to construct the insert 24 from a suitable rigid material, such as Deltrin™ nylon material, into whose surface 26 the at least one insert channel 28 can be machined. The number of insert channels 28 is not believed to be critical, so long as one or more of them are open in the direction of the proximal tube end 16, and can establish in the tracheal or endotracheal tube 14 a reverse venturi flow of the oxygen-containing gas away from the lungs 54 and bronchi 52 of the patient 48.

Figure 11:
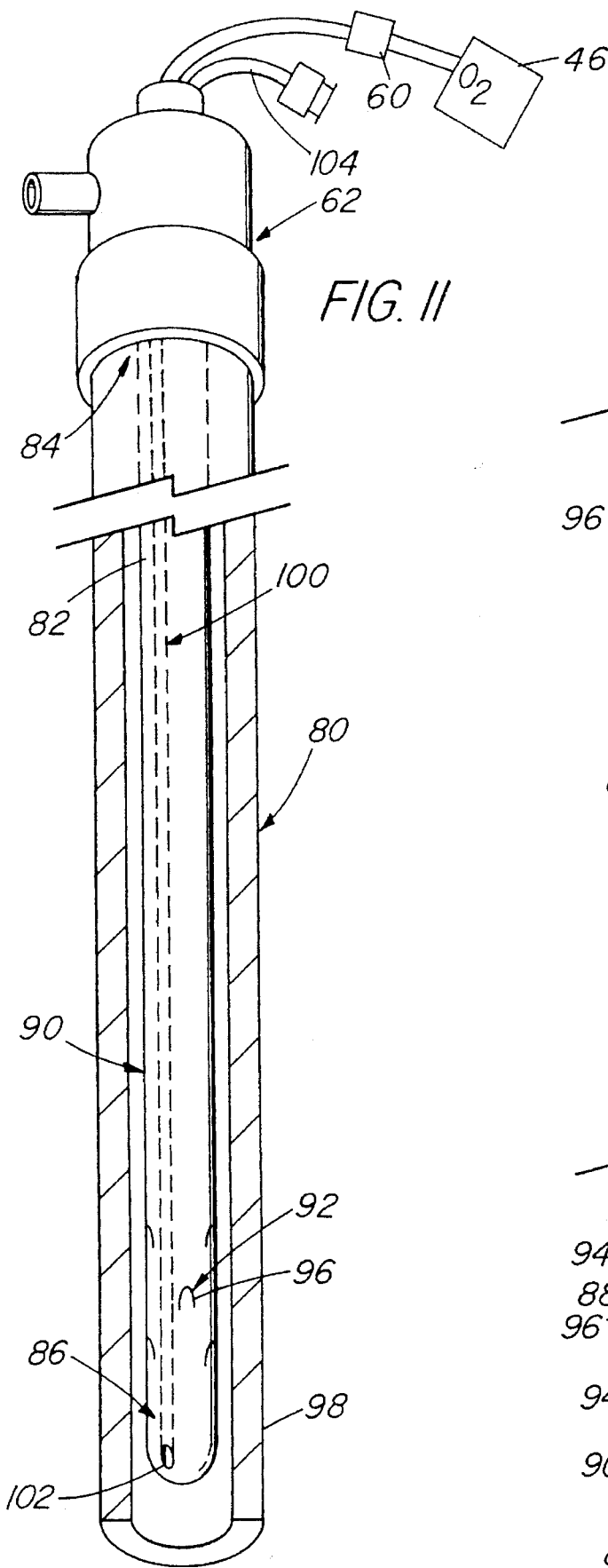
FIG. 11 is a side view of another preferred embodiment of the present invention.
Figure 12:
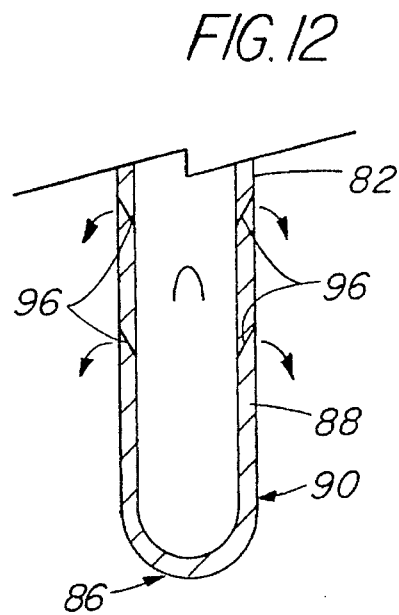
FIGS. 12 and 13 are partial views of the preferred embodiment of the present invention shown in FIG. 11.
Figure 13:
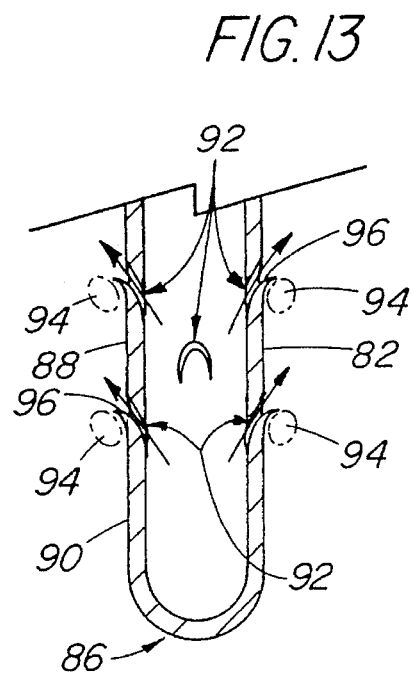

With reference now to FIGS. 11 through 13, a second embodiment of the present invention for creating a sub-atmospheric pressure near the carina 12 of a human or veterinary patient 48 is thereshown as a second device 80 which is positionable within the trachea 50 of the patient 48 in the same manner as shown in FIG. 1 with respect to the first device 10. The device 80 first comprises a hollow catheter 82 having a proximal catheter end 84 positioned outside the trachea 50 of the patient 48, and a closed distal catheter end 86 positioned within the trachea 50 of the patient 48, at or near the carina 12 of the patient 48. The device 80 also comprises a catheter sidewall 88 connected to and extending between the proximal catheter end 84 and the distal catheter end 86. The catheter sidewall 88 has an external surface 90 through which at least one perforation 92 is formed near the distal catheter end 86. The catheter sidewall 88 also includes a passageway 100 extending therethrough and has an outlet 102 distal of the at least one perforation 92 for infusing drugs and monitoring pressure near the carina of the patient. A side or end arm 104 with a well-known connector attached thereto communicates with passageway 100 for infusing drugs and monitoring pressure. The at least one perforation 92 is adapted for the passage of an oxygen-containing gas therethrough, for example, from a source 46 of the gas connected through a suitable valve 60 to a fitting or connector 62 at the proximal catheter end 84.

The at least one perforation 92 is acutely angled with respect to the external surface 90 of the catheter sidewall 88 and is open towards the proximal catheter end 84. The angle between the at least one perforation 92 (that is, the direction of the flow of the oxygen-containing gas through it) is advantageously no more than 45 degrees, is preferably less than 45 degrees, and is most preferably about 30 degrees. The at least one perforation 92 is preferably several in number and can be most conveniently formed as a plurality of slits 96 cut into the external surface 90 of the catheter sidewall 88, deep enough to allow the flow of the oxygen-containing gas from the source 46, through the interior of the catheter 82, and out the at least one perforation 92, that is, out the plurality of slits 96.

The catheter 82 is composed of a suitably flexible, medical grade material such as a nylon radiopaque material tubing, or a similar material which gives the catheter sidewall 88 an equivalent flexibility. The preferred plurality of slits 96 thereby form flexible flaps through which the oxygen-containing gas can flow; such flaps would prevent or limit the backflow of the gas, if it is supplied in a pulsed or periodically pressurized fashion.

The device 80 can further comprise a tracheal or endotracheal tube 98 in which the catheter 82 is positioned. The tube 98 can be a single lumen tube as shown, or can be a multiple lumen tube (not shown) like the multiple lumen tube 32 of the first device 10. In the latter case, the passageway within the wall of the multiple lumen tube can be used for monitoring pressure or gas composition, infusing drugs as previously described with respect to passageway 100 in catheter 82, or removing fluid.

With reference now to FIGS. 14 and 15, a third embodiment of the present invention for creating a sub-atmospheric pressure near the carina 12 of a human or veterinary patient 48 is thereshown as a third device 120 which is positionable within the trachea 50 of the patient 48 in the same manner as shown in FIG. 1 with respect to the first device 10. The device 120 is the embodiment of the present invention most closely related to the Kolobow catheter, and first comprises a hollow catheter 122 having a proximal catheter end 124, a distal catheter end 126 opposite the proximal catheter end 124, and an exterior catheter surface 128 extending between the proximal catheter end 124 and the distal catheter end 126. The catheter 122 has a defined catheter diameter near the distal catheter end, and the distal catheter end 126 has a shoulder 130 formed on it, extending radially outward of the catheter 122 a distance greater than the catheter diameter. In FIG. 14, the shoulder 130 is preferably annular in shape, and is conveniently formed by a plug 144 received in and sealed to, and thereby closing, the distal catheter end 126. Advantageously, the plug 144 includes a stem 146 received in the distal catheter end 126, and a rounded semispherical or bullet-shaped head 148 on the stem, the shoulder 130 then being formed as the base of the semispherical or bullet-shaped head 148. In FIG. 15, catheter 122 includes multiple passageways 150 and 152. Main passageway 150 has a closed distal end for delivering an oxygen-containing gas through the catheter wall, and second passageway 152 extends through the catheter with an outlet 154 at distal end 126 for infusing drugs and monitoring pressure near the carina 12 of a patient. The distal end of the catheter is heat tapered to form shoulder 130 and close main passageway 150. Second passageway 152 is maintained opened when heat tapering distal end 126.

The device 120 further comprises at least one radial perforation 132 through the catheter 122. The at least one radial perforation 132 is located adjacent to the distal catheter end 126, but is positioned between the proximal catheter end 124 and the shoulder 130 on the distal catheter end 126. The at least one radial perforation 132 is preferably several in number. The at least one radial perforation 132 is adapted for the passage of an oxygen-containing gas therethrough, for example, from a source 46 of the gas connected through a suitable valve 60 to a fitting or connector 62 at the proximal catheter end 124. In FIG. 15, device 120 further includes an end arm 156 that is connected to connector 62 and communicates with second passageway 152.

The device 120 also comprises a tubular member 134 positioned about the exterior catheter surface 128, adjacent to the distal catheter end 126 and extending over the at least one radial perforation 132. The tubular member 134 has a distal member end 136 which abuts the shoulder 130 of the distal catheter end 126 and which is substantially sealed to the exterior catheter surface 128, but which does not cover or seal the at least one radial perforation 132. "Substantially sealed" means merely that any flow of the oxygen-containing gas out the distal member end 136 is insufficient to prevent establishment of the desired reverse venturi effect. The tubular member 134 also has a proximal member end 138 opposite the distal member end 136.

Unlike the distal member end 136, the proximal member end 138 has an interior diameter greater than the defined catheter diameter. A gap 140 is thus provided between the tubular member 134 and the exterior catheter surface 128, in fluid communication with the at least one radial perforation 132 through the catheter 122. The flow of the oxygen-containing gas through the catheter 122, the at least one radial perforation 132 and the gap 140 provides the reverse venturi in this embodiment.

Manipulation of the tubular member 134 to give its proximal and distal ends 138 and 136 different diameters can be achieved in a remarkably elegant yet simple manner. Most easily, the tubular member is composed of a shrink-wrap tubing having a manufactured diameter greater than the diameter of the catheter 122, yet having a diameter after heat-shrinking no greater than, and preferably less than, the diameter of the catheter 122. The application of heat to only the distal member end 136 shrinks the distal member end 136 closely about the exterior catheter surface 128, and preferably substantially seals the distal member end 136 to the exterior catheter surface 128; while the proximal member end 138 is unheated and retains its original diameter, and is thereby spaced from the exterior catheter surface 128 to create the gap 140. Roughening or abrading the abutting portion of the exterior catheter surface 128 prior to the introduction of the tubular member 134 over the catheter 122 can facilitate such sealing, as can the use of a suitable medical grade adhesive.

The device 120 can further comprise a tracheal or endotracheal tube (not shown, but a tube such as the tube 98 of FIG. 11) in which the catheter 122 is positioned. The tube can be a single lumen tube, or can be a multiple lumen tube like the multiple lumen tube 32 of the first device 10. In the latter case, the passageway within the wall of the multiple lumen tube can be used either for monitoring pressure or gas composition, infusing drugs, or removing fluid by suction.

It is important to recognize that the use of the shoulder 130 to secure the tubular member 134 on the catheter 122 is a significant, practical improvement to the Kolobow reverse venturi catheter. First, the shoulder 130 provides a physical barrier to prevent the tubular member 134 from sliding off the catheter 122 in a distal direction, should the attachment or adhesion of the tubular member 134 to the catheter 122 fail. Secondly, any element forming the shoulder 130 (preferably, the plug 144 of FIG. 14 or the tapered distal end of FIG. 15) can be more reliably secured to the distal catheter end 126, than can the tubular portion 19 of Kolobow be secured to the catheter tip 16 of Kolobow. Again, the reason for this is a practical one; it is easier to securely and reliably affix a rigid object (the stem 146 of the plug 144 of FIG. 14 or the heat tapered distal end of FIG. 15) inside the end of a hollow tube of one or two millimeters diameter (the distal catheter end 126) than it is to affix a rigid object (the catheter tip 16 of Kolobow) over the end of a flexible hollow tube of one or two millimeters diameter (the catheter of Kolobow).

Use of the present invention in ventilation procedures such as ITV and ITPV can now be easily understood. The passage of an oxygen-containing gas from the source 46, through any of the devices 10, 80 and 120, and out their respective channels 28, perforations 92 or gap 140, creates during exhalation a respective zone 30 (device 10, FIG. 10), 94 (device 80, FIG. 13) or 142 (device 120, FIG. 14 or 15) of sub-atmospheric pressure. Taking the device 10 as an example, in operation the device 10 is positioned with respect to the patient 48 so that the distal tube end 18 lies at the level of the carina 12. (The distal catheter end 86 of the device 80 or the distal catheter end 126 of the device 120 would be positioned similarly, either with or without a surrounding tracheal or endotracheal tube 98.) A moist, warmed oxygen-containing gas is then introduced into the device 10 from the source 46, through the valve 60, and allowed to flow out the at least one insert channel 28, such as the circumferential channel 36 and the plural axial channels 38. During the inhalation phase of the respiratory cycle, as shown by the arrows in FIG. 9 the gas passes into the bronchi 52 and the lungs 54, oxygenating the lungs 54 in the desired manner. During the exhalation phase of the respiratory cycle, as shown by the arrows in FIG. 10, the oxygen-containing gas continues to flow out of the channels 36 and 38 and creates the zones 30 of sub-atmospheric pressure which aid removal of the carbon-dioxide laden air from the lungs 54 and bronchi 52. It is critical to achieving this reverse venturi that the oxygen-containing gas flow through the device 10 at some time during the exhalation phase, preferably continuously. As indicated, the devices 80 and 120 are used in a similar manner.

The devices 10, 80 and 120 of the present invention may be used either with or without conventional mechanical ventilation (MV). The details of use would be comparable to those disclosed in the Kolobow patent at column 3, line 48, through column 4, line 54, which are expressly incorporated by herein. Indeed, any of the devices 10, 80 and 120 of the present invention may be used by substitution in any of the ventilation methods disclosed in the Kolobow patent. More particularly, the devices 10, 80 and 120 may be used in such methods in place of the catheter 1 shown in FIGS. 1 through 3C of the specification of that patent. The use of the devices 10, 80 and 120 is not limited to the constant-flow methods of the patent specification, however, and the present invention is expected to be useful in ventilation methods in which the flow rate or pressure varies during the ventilation cycle, so long as a sufficient flow rate through the devices 10, 80 and 120 is provided to create sub-atmospheric pressure adjacent to the devices during patient exhalation, and aid removal of carbon-dioxide enriched air from the lungs of the patient. Constant-flow methods are probably preferred, however.

The devices 10, 80 and 120 share the many advantages of the Kolobow reverse venturi catheter. They reduce the size of the dead space in the trachea which might trap carbon-dioxide laden air in the lungs and bronchi, or which might block the introduction of oxygen into the bronchi and lungs. They also permit ventilation procedures to be successfully carried out with lower gas flow rates and lower peak respiratory pressures, reducing the risk of trauma to the lungs, and the other problems mentioned above.

The other details of the construction or composition of the various elements of the disclosed embodiments of the present invention are not believed to be critical to the achievement of the advantages of the present invention, so long as the elements possess the strength or flexibility needed for them to perform as disclosed. The selection of these and other details of construction are believed to be well within the ability of one of even rudimentary skills in this area, in view of the present disclosure.

Industrial Applicability

The present invention is useful in the performance of ventilation procedures, and therefore finds applicability in human and veterinary medicine.

It is to be understood, however, that the above-described device is merely an illustrative embodiment of the principles of this invention, and that other devices and methods for using them may be devised by those skilled in the art, without departing from the spirit and scope of the invention. It is also to be understood that the invention is directed to embodiments both comprising and consisting of the disclosed parts.

What is claimed is:

1. A device (10) for creating a sub-atmospheric pressure near a patient's carina (12), comprising:

a tracheal or endotracheal tube (14) having a proximal tube end (16), a distal tube end (18) spaced from the proximal tube end (16), a tube wall (20) connected to and extending between the proximal tube end (16) and the distal tube end (18), and a tube passageway (22) for the flow of an oxygen-containing gas; and an insert (24) received in and circumferentially abutted by the distal tube end (18), the insert (24) having a surface (26) defining at least one insert channel (28) in communication with the tube passageway (22), and the at least one insert channel (28) being open towards the proximal tube end (16);

such that a zone (30) of sub-atmospheric pressure is established, inside the tracheal or endotracheal tube (14) adjacent the distal tube end (18) during patient exhalation, upon passage of an oxygen-containing gas through the tube passageway (22) and the at least one insert channel (28).

2. The device (10) according to claim 1, wherein the tracheal or endotracheal tube (14) is a multiple lumen tube (32), and wherein the tube passageway (22) is formed in the tube wall (20) and includes a passageway outlet (34) adjacent the distal tube end (18).

3. The device (10) according to claim 2, wherein the at least one insert channel (28) comprises a circumferential channel (36) in communication with the passageway outlet (34).

4. The device (10) according to claim 2, wherein the at least one insert channel (28) comprises a plurality (38) of axial channels and a circumferential channel (36) connecting the plurality of axial channels and the tube passageway outlet (34).

5. The device (10) according to claim 2, wherein the multiple lumen tube (32) includes a second tube passageway (64) formed in the tube wall (20) and includes a second passageway outlet (66) distal the insert (24).

6. The device (10) according to claim 1, wherein the insert (24) is a hollow cylinder (40).

7. The device (10) according to claim 6, wherein the hollow cylinder (40) includes an outer surface (42), and wherein the at least one insert channel (28) is formed on the outer surface (42) of the cylinder (40).

8. The device (10) according to claim 1, wherein the insert surface (26) defining the at least one insert channel (28) is the outer surface (42) of the insert (24), wherein the tracheal or endotracheal tube wall (20) includes an inner surface (44), and wherein the at least one channel (28) is further defined by the inner surface (44) of the tracheal or endotracheal tube wall (20).

9. A device (10) for creating a sub-atmospheric pressure near a patient's carina (12), comprising:

a multiple lumen tracheal or endotracheal tube (32) having a proximal tube end (16), a distal tube end (18) spaced from the proximal tube end (16), a tube wall (20) connected to and extending between the proximal tube end (16) and the distal tube end (18), and a tube passageway (22) formed in the tube wall (20) for the flow of an oxygen-containing gas, the tube passageway (22) including a passageway outlet (34) adjacent the distal tube end (18); and an insert (24) received in and circumferentially abutted by the distal tube end (18), the insert (24) being shaped as a hollow cylinder (40), and the insert (24) having an outer surface (42) defining a plurality of axial channels (38) and a circumferential channel (36) connecting the axial channels (38) and the tube passageway (22), the plurality of axial channels (38) being open towards the proximal tube end (16);

wherein the tracheal or endotracheal tube wall (20) includes an inner surface (44), and wherein the axial and circumferential channels (38 and 36) are further defined by the inner surface (44) of the tube wall (20);

such that a zone (30) of sub-atmospheric pressure is established, inside the multiple lumen tracheal or endotracheal tube (32) adjacent the distal tube end (18) during patient exhalation, upon passage of an oxygen-containing gas through the tube passageway (22), the circumferential channel (36), and the plurality of axial channels (38).

10. A device (80) for creating a sub-atmospheric pressure near a patient's carina (12), comprising:

a catheter (82) having a proximal catheter end (84), a closed distal catheter end (86) opposite the proximal catheter end (84), and a catheter sidewall (88) connected to and extending between the proximal catheter end (84) and the distal catheter end (86), the catheter sidewall (88) having an external surface (90); and at least one perforation (92) through the catheter sidewall (88) near the distal catheter end (86);

wherein the at least one perforation (92) is acutely angled with respect to the external surface (90) of the catheter sidewall (88) and being open towards the proximal catheter end (84), such that a zone (94) of sub-atmospheric pressure is established, outside the catheter (82) adjacent the distal catheter end (86) during patient exhalation, upon passage of an oxygen-containing gas through the catheter (82) and the at least one perforation (92).

11. The device (80) according to claim 10, wherein the at least one perforation (92) is formed by a slit (96) cut into the external surface (90) of the catheter sidewall (88).

12. The device (80) according to claim 11, wherein the slit (96) is cut at an angle of less than 45 degrees with respect to the external surface (90) of the catheter sidewall (88).

13. The device (80) according to claim 11, wherein the catheter sidewall (88) possesses a flexibility equivalent to the flexibility of nylon radiopaque material tubing.

14. The device (80) according to claim 10, wherein the at least one perforation (92) is angled less than 45 degrees with respect to the external surface (90) of the catheter sidewall (88).

15. The device (80) according to claim 10, further comprising a tracheal or endotracheal tube (98) in which the catheter (82) is positioned.

16. The device (80) according to claim 10, wherein the catheter includes a passageway (100) formed in the catheter sidewall (88) and includes an outlet (102) distal the at least one perforation (92).

17. A device (120) for creating a sub-atmospheric pressure near a patient's carina (12), comprising:

a catheter (122) having a proximal catheter end (124), a distal catheter end (126) opposite the proximal catheter end (124), and an exterior catheter surface (128) extending between the proximal catheter end (124) and the distal catheter end (126), the catheter (122) having a defined catheter diameter near the distal catheter end (126), and the distal catheter end (126) having a shoulder (130) extending radially outward of the catheter (122) a distance greater than the defined catheter diameter;

at least one radial perforation (132) through the catheter (122), located adjacent the distal catheter end (126) but between the proximal catheter end (124) and the shoulder (130) on the distal catheter end (126); and a tubular member (134) positioned about the exterior catheter surface (128) and extending over the at least one radial perforation (132), the tubular member (134) including a distal member end (136) which abuts the shoulder (130) of the distal catheter end (126) and which is substantially sealed to the exterior catheter surface (128), and a proximal member end (138) opposite the distal member end (136) having an interior diameter greater than the defined catheter diameter, so as to provide a gap (140) between the tubular member (134) and the exterior catheter surface (128) such that a zone (142) of sub-atmospheric pressure is established, outside the catheter (122) adjacent the distal catheter end (126) during patient exhalation, upon passage of an oxygen-containing gas through the catheter (122), the at least one perforation (132), and the gap (140) between the tubular member (134) and the exterior catheter surface (128).

18. The device (120) according to claim 17, wherein the shoulder (130) on the distal catheter end (126) is annular in shape.

19. The device (120) according to claim 17, wherein the shoulder (130) on the distal catheter end (126) is formed by a plug (144) received in and sealed to the distal catheter end (126).

20. The device (120) according to claim 17, wherein the tubular member (134) is formed of shrink-wrap tubings shrunk at the distal member end (136) about the exterior catheter surface (128).

21. The device (120) according to claim 17, wherein the catheter includes a passageway (152) extending therethrough and including a passageway outlet (154) distal the at least one radial perforation (132).

22. The device (120) according to claim 17, further comprising a tracheal or endotracheal tube (98) in which the catheter (122) is positioned.

* * * * *